(12) United States Patent
Kankan et al.

(10) Patent No.: US 7,772,394 B2
(45) Date of Patent: Aug. 10, 2010

(54) ZALEPLON SYNTHESIS

(75) Inventors: Rajendra Narayanrao Kankan, Maharashtra (IN); Dharmaraj Ramachandra Rao, Maharashtra (IN)

(73) Assignee: Cipla Limited, Mumbai, Maharashtra (IN)

( * ) Notice: Subject to any disclaimer, the term of this patent is extended or adjusted under 35 U.S.C. 154(b) by 601 days.

(21) Appl. No.: 10/570,453

(22) PCT Filed: Sep. 2, 2004

(86) PCT No.: PCT/GB2004/003757

§ 371 (c)(1),
(2), (4) Date: Oct. 18, 2006

(87) PCT Pub. No.: WO2005/023813

PCT Pub. Date: Mar. 17, 2005

(65) Prior Publication Data

US 2007/0191399 A1    Aug. 16, 2007

(30) Foreign Application Priority Data

Sep. 4, 2003    (IN) .................. 913/MUM/2003

(51) Int. Cl.
C07D 487/04    (2006.01)
A61K 31/519    (2006.01)
(52) U.S. Cl. .................. 544/281; 514/259.3
(58) Field of Classification Search .............. 544/281; 514/259.3
See application file for complete search history.

(56) References Cited

U.S. PATENT DOCUMENTS

| | | |
|---|---|---|
| 4,626,538 A | 12/1986 | Dusza et al. |
| 6,884,888 B2 * | 4/2005 | Korodi et al. ............... 544/281 |
| 7,034,155 B2 | 4/2006 | Horns |
| 2002/0072527 A1 | 6/2002 | Aslam et al. |
| 2002/0072605 A1 | 6/2002 | Tombari et al. |
| 2003/0040522 A1 | 2/2003 | Korodi et al. |

FOREIGN PATENT DOCUMENTS

| | | |
|---|---|---|
| CZ | 292 869 B | 6/2003 |
| EP | 0 776 898 A1 | 6/1997 |
| WO | WO 02/12244 A2 | 2/2002 |
| WO | WO 02/100828 A2 | 12/2002 |
| WO | WO 03/011228 A2 | 2/2003 |
| WO | WO 03/068775 A1 | 8/2003 |

OTHER PUBLICATIONS

Jacobs, A. "Understanding Organic Reactions Mechanisms," 1997, p. 131.*
STN printout, abstract, Hradil et. al., CZ 292869, pp. 1-2.*
STN printout, abstract, Hradil et. al., CZ 292869, pp. 1-2, 2003.*
International Search Report and Written Opinion, PCT/GB2004/003757, Nov. 29, 2004, 10 pgs.
International Preliminary Report on Patentability, PCT/GB2004/003757, Sep. 6, 2005, 7 pgs.

* cited by examiner

*Primary Examiner*—James O Wilson
*Assistant Examiner*—Susanna Moore
(74) *Attorney, Agent, or Firm*—Conley Rose, P.C.; Rodney B. Carroll

(57) ABSTRACT

A process for making zaleplon comprising alkylating 3-[3-(dimethylamino)-1-oxo-2-propenyl]-phenyl]-acetamide with ethyl iodide in the presence of an alkali metal hydroxide or alkoxide selected from sodium hydroxide, potassium hydroxide, sodium methoxide, sodium tert-butoxide or potassium tert-butoxide in an aprotic solvent to give N-ethyl-[3-[3-(dimethylamino)-1-oxo-2-propenyl]-phenyl]-acetamide, condensing N-ethyl-[3-[3-(dimethylamino)-1-oxo-2-propenyl]-phenyl]-acetamide and 3-amino-4-cyanopyrazole, and isolating zaleplon from the reaction. Preferably, the condensing is done in the presence of (a) a water immiscible organic acid; (b) a cation exchange resin; or (c) a water miscible organic acid in water or in a C-1 to C-4 alcohol or in a mixture of water and a C-1 to C-4 alcohol.

19 Claims, 1 Drawing Sheet

Fig I
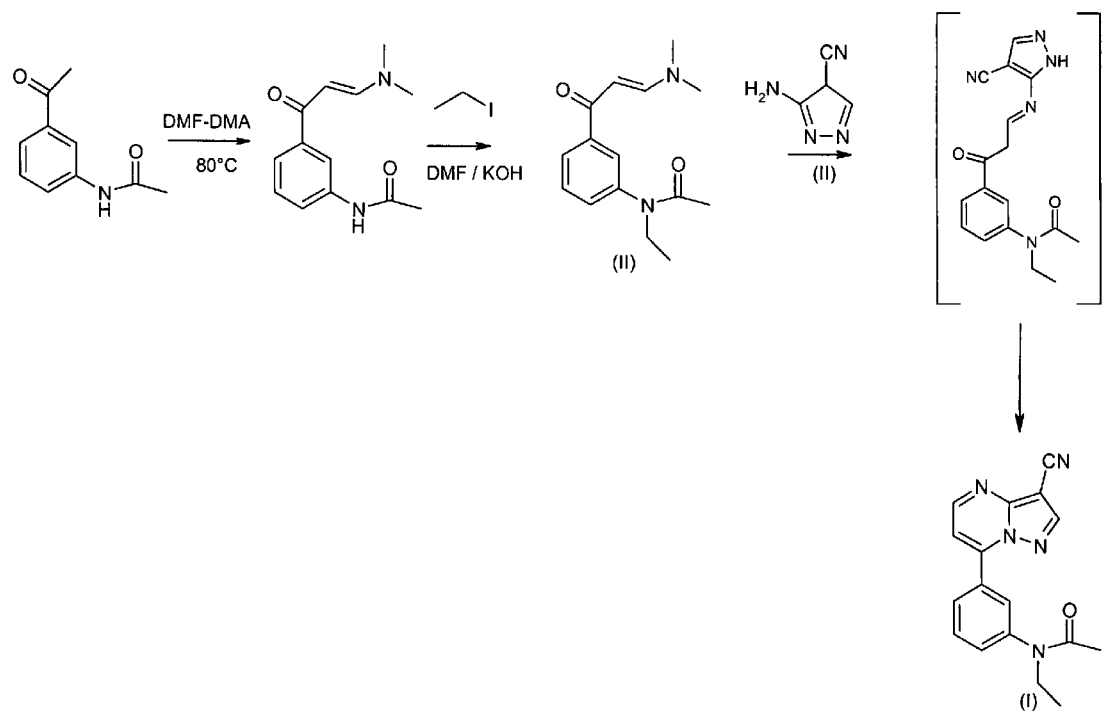

ZALEPLON SYNTHESIS

The present invention relates to a process for making N-[3-(3-cyanopyrazolo-[1,5-a]-pyrimidin-7-yl)-phenyl]-N-ethyl acetamide known as zaleplon, and to pharmaceutical compositions comprising zaleplon so made. The compound possesses anxiolytic, antiepileptic, sedative & hypnotic properties. It is also used in the treatment of insomnia.

Various prior art patents report the synthesis of zaleplon. U.S. Pat. No. 4,626,538 discloses novel N-[3-(3-cyanopyrazolo[1,5-a]pyrimidin-7-yl)phenyl]-N-ethyl acetamide compounds and a process for the synthesis of these. The patent discloses the final step cyclisation of 3-amino 4-cyano pyrazole with N-ethyl-[3-[3-(dimethylamino)-1-oxo-2-propenyl]-phenyl]-acetamide in acetic acid to give zaleplon. N-ethyl-[3-[3-(dimethylamino)-1-oxo-2-propenyl]-phenyl]-acetamide is prepared by N-alkylation of 3-[3-(dimethylamino)-1-oxo-2-propenyl]-phenyl]-acetamide with ethyl iodide in the presence of sodium hydride. Alternatively 3-(3-cyanopyrazolo-[1,5-a]-pyrimidin-7-yl)-phenyl]-acetamide is alkylated with ethyl iodide in the presence of sodium hydride, alkoxides and the like to give zaleplon. This process leads to formation of impurities and gives a very low yield of zaleplon.

EP0776898 describes an improved process for large-scale production of zaleplon. It describes a reaction between 3-dimethylamino-1-(3-N-ethyl-N-acetylaminophenyl)-2-propen-1-one and 3-amino-4-cyano pyrazole or a suitable salt thereof in a mixture comprising water and acetic acid. Improved yields, a decrease in reaction time and purity is achieved by adding water to the acetic acid. The method described also works utilizing salts of either or both starting materials.

WO 02/12244 discloses novel crystalline polymorphic forms of zaleplon namely Forms I, II and III and methods for their preparation. Form I is an anhydrous crystal form, while forms II and III are crystalline forms which can be anhydrous or hydrates.

US 2002/0072527 provides a process for the production of zaleplon that involves reacting N-[3-[3-(dimethylamino)-1-oxo-2-propenyl]-phenyl]-N-ethyl acetamide or a salt thereof with 3-amino-4-cyano pyrazole or a salt thereof under acidic conditions in a reaction medium comprising a mixture of water and a water miscible organic compound.

WO 02100828 describes a process for purifying zaleplon and crystalline forms of zaleplon. This invention also describes a purification process of separating zaleplon and regioisomer that tends to form as a byproduct in the synthesis of zaleplon.

WO 03/011228 relates to novel crystalline polymorphic forms of zaleplon and a method for the preparation thereof, and their therapeutic uses.

US 2003040522 describes a process for making zaleplon which involves reacting N-[3-(3-cyanopyrazolo)-1-oxo-2-propenyl)phenyl]-N-ethyl acetamide or a salt thereof with 3-amino-4-cyanopyrazole or a salt thereof under acidic conditions in a reaction medium comprising a mixture of water and a water-miscible organic compound.

We have found that the prior art processes have drawbacks in terms of either yield or the level of impurities (or both), particularly for industrial-scale production: we have now devised an improved process which minimises these problems.

According to the present invention, there is provided a process for malking zaleplon, which process comprises
  i. alkylating 3-[3-(dimethylamino)-1-oxo-2-propenyl]-phenyl]-acetamide with ethyl iodide in the presence of an alkali metal hydroxide or alkoxide in an aprotic solvent to give N-ethyl-[3-[3-(dimethylamino)-1-oxo-2-propenyl]-phenyl]-acetamide;
  ii. condensing of N-ethyl-[3-[3-(dimethylamino)-1-oxo-2-propenyl]-phenyl]-acetamide and 3-amino-4-cyanopyrazole;
  iii. isolating zaleplon from the reaction.

Preferably, the condensing is done in the presence of (a) a water immiscible organic acid; (b) a cation exchange resin; or (c) a water misible organic acid in water or in a C-1 to C-4 alcohol or in a mixture of water and a C-1 to C-4 alcohol;

Syntheses of N-[3-[3-(Dimethylamino)-1-oxo-2-propenyl]phenyl]-N-ethyl acetamide so far described use strong bases such as sodium hydride for the alkylation of 3-[3-(dimethylamino)-1-oxo-2-propenyl]-phenyl]-acetamide formed by refluxing 3-acetamidoacetophenone with dimethyl formamide-dimethyl acetal. The present invention discloses an improved method for the N-alkylation of 3-[3-(dimethylamino)-1-oxo-2-propenyl]-phenyl]-acetamide, which method uses milder bases. In particular, hydroxides and alkoxides of alkali metals are employed.

Cyclisation of 3-amino 4-cyano pyrazole with N-ethyl-[3-[3-(dimethylamino)-1-oxo-2-propenyl]-phenyl]-acetamide in acetic acid gives zaleplon. This process leads to formation of impurities and gives a very low yield of zaleplon.

The cyclisation is described in various prior art processes to proceed under acidic conditions by either use of acid solvents such as acetic acid, or use of various organic or inorganic acids in water or in a mixture of water and a water miscible solvent. The use of the corresponding salts of these intermediates has also been described.

The present invention provides a simple, efficient and novel method for preparation of zaleplon by making use of water immiscible organic acids and suitable solvents for carrying out the cyclisation reaction between 3-amino 4-cyano pyrazole and N-ethyl-[3-[3-(dimethylamino)-1-oxo-2-propenyl]-phenyl]-acetamide.

In one embodiment, the invention also comprises cyclisation of 3-amino 4-cyano pyrazole and N-ethyl-[3-[3-(dimethylamino)-1-oxo-2-propenyl]-phenyl]-acetamide in the presence of a cation exchange resin in a suitable solvent or solvents.

The process of the present invention leads to formation of low levels of impurities and gives very high yields of zaleplon.

In a preferred embodiment, the present invention comprises alkylating 3-[3-(dimethylamino)-1-oxo-2-propenyl]-phenyl]-acetamide with ethyl iodide in the presence of an alkali metal hydroxide or alkoxide in a polar aprotic solvent at ambient temperature (eg 20° C. to 30° C.). More preferably, the present invention comprises alkylating 3-[3-(dimethylamino)-1-oxo-2-propenyl]-phenyl]-acetamide with ethyl iodide in the presence of sodium hydroxide or potassium hydroxide using dimethyl formamide as a solvent at temperatures ranging from 10° C. to 100° C., more preferably between 20° C. to 30° C.

In an alternative embodiment, the invention comprises alkylating 3-[3-(dimethylamino)-1-oxo-2-propenyl]-phenyl]-acetamide with ethyl iodide in the presence of sodium methoxide or potassium t-butoxide using dimethyl formamide as a solvent at temperatures ranging from 10° C. to 100° C., more preferably between 20° C. to 30° C.

Condensation between N-[3-[3-(Dimethylamino)-1-oxo-2-propenyl]-phenyl]-N-ethyl acetamide (II) and 3-amino-4-cyanopyrrazole (III) requires acidic condition and it proceeds through formation of an intermediate imine product. The imine on further treatment under acidic conditions gives Zaleplon (I) as depicted in FIG. 1.

In another preferred embodiment, the present invention comprises condensing and cyclising N-[3-[3-(Dimethylamino)-1-oxo-2-propenyl]-phenyl]-N-ethyl acetamide and 3-amino-4-cyanopyrrazole using water immiscible acids, preferably organic acids, in aqueous solvents or water miscible organic acids in non-aqueous solvents.

The condensation and cyclisation reaction described may comprise using water insoluble organic acids or cation exchange resins in suitable solvents at ambient (20° C. to 30° C., for example) to reflux temperatures. Water miscible organic acids may also be used.

Suitable acids that may be used for the condensation reaction include edetic acid, fumaric acid, benzoic acid, and salicylic acid.

The condensation and cyclisation may, if desired, also be performed using a strong cation exchange resin, preferably one containing sulphonic acid groups. Protic polar solvents are preferably used.

The reaction is generally completed from 20 min to 48 hrs depending on the acid used.

The following examples illustrate the invention.

EXAMPLE 1

Preparation of N-[3-[3-(Dimethylamino)-1-oxo-2-propenyl]-phenyl]-N-ethyl acetamide 36.2 gm Powdered potassium hydroxide was added portion wise to a clear solution of a mixture of 100 gm N-[3-[3-(Dimethylamino)-1-oxo-2-propenyl]phenyl] acetamide and 70 ml ethyl iodide in 1000 ml of dimethyl formamide at 39°-42° C. over 60 min. the reaction mixture was stirred for 6 hrs. after completion, the reaction mixture was quenched in water and extracted in dichloromethane. The dichloromethane layer was washed with water, dried over sodium sulphate and concentrated to get oil, which upon trituration in hexane gave a solid product which was filtered and dried at 40° C. under vacuum to give the title compound.

EXAMPLE 2

Preparation of N-[3-[3-(Dimethylamino)-1-oxo-2-propenyl]-phenyl]-N-ethyl acetamide 4.25 gm of Potassium tert-butoxide was added portion wise to a clear solution of 5 gm N-[3-[3-(Dimethylamino)-1-oxo-2-propenyl]-phenyl] acetamide in 50 ml dimethyl formamide. A solution of 5.25 gm Ethyl iodide in 20 ml dimethyl formamide was added drop wise over 3 hrs. at 35° C.-40° C. The reaction mass was stirred for 6 hrs and then quenched in 300 ml of water and extracted in dichloromethane. The organic layer was washed with water, dried over sodium sulphate and concentrated under vacuum to get oil, which was dissolved in 5 ml dichloromethane and 50 ml hexane was added to precipitate the product. The solids obtained was filtered and washed with hexane and dried in vacuum tray dryer at 35° C. for 6 hrs.

EXAMPLE 3

Preparation of N-[3-[3-(Dimethylamino)-1-oxo-2-propenyl]phenyl]-N-ethyl acetamide 17.5 gm Sodium methoxide was added portion wise to a clear solution of 50 gm N-[3-[3-(Dimethylamino)-1-oxo-2-propenyl]-phenyl] acetamide and 85 gm ethyl iodide in 500 ml dimethyl formamide. After 6 hrs of stirring at room temperature, the reaction mass was quenched in 5 liters of water and extracted in dichloromethane. The dichloromethane layer was washed with water, dried over sodium sulphate and concentrated under vacuum to get oil, which upon trituration in hexane gave the title product as a solid.

EXAMPLE 4

Preparation of N-[3-(3-cyanopyrazolo-[1,5-a]-pyrimidin-7-yl)-phenyl]-N-ethyl acetamide 2.0 gm N-[3-[3-(Dimethylamino)-1-oxo-2-propenyl]phenyl]-N-ethyl acetamide was added to a slurry of 40 ml water containing 0.83 gm of 3-amino-4-cyanopyrazole and 6.0 gm edetic acid. The reaction mass was heated to 60° C. for 3 hrs. After cooling the reaction mixture to 20° C., 15% aqueous sodium hydroxide solution was added and the pH of the reaction mixture was adjusted to between 9-10. The reaction mass was stirred for 1 hr. and filtered to give the title compound.

EXAMPLE 5

Preparation of N-[3-(3-cyanopyrazolo-[1,5-a]-pyrimidin-7-yl)-phenyl]-N-ethyl acetamide 0.83 gm 3-amino-4-cyanopyrazole was added to the solution of 40 ml water containing 2 gm N-[3-[3-(Dimethylamino)-1-oxo-2-propenyl]phenyl]-N-ethyl at room temp. 6 gm fumaric acid was charged and reaction mass was heated to 60° C. for 3 hrs. After cooling to 20° C., 15% aqueous sodium hydroxide solution was added and pH of the reaction mixture adjusted to between 9-10. The reaction mass was stirred for 1 hr. and filtered to give the title compound.

EXAMPLE 6

Preparation of N-[3-(3-cyanopyrazolo-[1,5a]-pyrimidin-7-yl)-phenyl]-N-ethyl acetamide 10 gm of Amberlite AR 120 resin ($H^+$) form was added to 2 gm of N-[3-[3-(Dimethylamino)-1-oxo-2-propenyl]-phenyl]-N-ethyl acetamide and 1.16 gm of 3-amino-4-cyanopyrazole in 20 ml water. The reaction mass was stirred at room temperature for 48 hrs, filtered and extracted in dichloromethane. The organic layer was washed with water, dried over sodium sulphate and filtered. To the clear dichloromethane solution, 120 ml hexane was added and the mixture stirred for 24 hours to give the title compound as a solid.

EXAMPLE 7

Preparation of N-[3-(3-cyanopyrazolo-[1,5a]-pyrimidin-7-yl)-phenyl]-N-ethyl acetamide 2 gm of N-[3-[3-(Dimethylamino)-1-oxo-2-propenyl]-phenyl]-N-ethyl acetamide and 1 gm of 3-amino-4-cyanopyrazole was dissolved in 10 ml methanol. 12 gm Amberlite AR 120 resin ($H^+$ form) was added as a slurry with 10 ml water. The reaction mass was refluxed for 5 hrs. and cooled to 25° C. and filtered and the solids washed with methanol. 30 ml water is added to the clear filtrate and the mixture stirred for 30 mts. The precipitated product was filtered to give the title product.

EXAMPLE 8

Preparation of N-[3-(3-cyanopyrazolo-[1,5a]-pyrimidin-7-yl)-phenyl]-N-ethyl acetamide 43.75 gm maleic acid was added to a solution of 13 gm 3-amino-4-cyanopyrazole and 25 gm N-[3-[3-(Dimethylamino)-1-oxo-2-propenyl]phenyl]-N-ethyl acetamide in 125 ml absolute alcohol. The reaction mass was heated to 60° C. for 30 min and 625 ml water was added at same temp. The reaction mixture was cooled gradually to 25° C. and stirred for 6 hrs. The precipitated product was filtered to give the title product.

EXAMPLE 9

Preparation of N-[3-(3-cyanopyrazolo-[1,5a]-pyrimidin-7-yl)-phenyl]-N-ethyl acetamide 37.5 gm maleic acid was added to a solution of 4.15 gm 3-amino-4-cyanopyrazole and 25 gm N-[3-[3-(Dimethylamino)-1-oxo-2-propenyl]-phenyl]-N-ethyl acetamide in 250 ml of methanol. The reaction mass was heated to 65° C. for 8 hrs and 250 ml water was added at same temp. The reaction mixture was cooled gradually to 25° C. and stirred for 6 hrs. The precipitated product was filtered and dried to give the title compound.

EXAMPLE 10

Preparation of N-[3-(3-cyanopyrazolo-[1,5a]-pyrimidin-7-yl)-phenyl]-N-ethyl acetamide 3 gm N-[3-[3-(Dimethylamino)-1-oxo-2-propenyl]phenyl]-N-ethyl acetamide was charged to the solution of 1.24 gm of 3-amino-4-cyanopyrazole in 30 ml water. To this, 4.5 gm maleic acid dissolved in 20 ml water was added at 60° C. drop wise in 10 min. the reaction mass was stirred for 2 hrs at same temperature and cooled gradually to 25° C. The precipitated product was filtered and dried to give the title compound

EXAMPLE 11

A capsule comprising zaleplon was prepared in accordance with the following table.

| Sr. no | Ingredients | Qty/cap |
|---|---|---|
| 1. | Zaleplon | 5.00 |
| 2. | Starch | 30.00 |
| 3. | Lactose monohydrate | 57.10 |
| 4. | Sodium lauryl sulphate | 7.50 |
| 5. | Magnesium stearate | 0.40 |
| 6. | Empty hard gelatin capsules | . . . |

Cosift 1, 2, 4 to form premix 1. Blend premix 1 with 3. Lubricate with 5 and fill in capsules.

The invention claimed is:

1. A process for making zaleplon, comprising:
   i. alkylating 3-[3-(dimethylamino)-1-oxo-2-propenyl]-phenyl]-acetamide with ethyl iodide in the presence of an alkali metal hydroxide or alkoxide selected from sodium hydroxide, potassium hydroxide, sodium methoxide, sodium tert-butoxide or potassium tert-butoxide in an aprotic solvent to give N-ethyl-[3-[3-(dimethylamino)-1-oxo-2-propenyl]-phenyl]-acetamide;
   ii. condensing N-ethyl-[3-[3-(dimethylamino)-1-oxo-2-propenyl]phenyl]-acetamide and 3-amino-4-cyanopyrazole, wherein the condensing is done in the presence of (a) a water immiscible organic acid, wherein the water immiscible acid used for the condensation reaction is edetic acid, fumaric acid, salicyclic acid or benzoic acid; (b) a cation exchange resin; or (c) a water miscible organic acid in water or in a C-1 to C-4 alcohol or in a mixture of water and a C-1 to C-4 alcohol; and
   iii. isolating zaleplon from the reaction.

2. A process for making zaleplon, comprising:
   i. alkylating 3-[3-(dimethylamino)-1-oxo-2-propenyl]-phenyl]-acetamide with ethyl iodide in the presence of an alkali metal hydroxide or alkoxide selected from sodium hydroxide, potassium hydroxide, sodium methoxide, sodium tert-butoxide or potassium tert-butoxide in an aprotic solvent to give N-ethyl-[3-[3-(dimethylamino)-1-oxo-2-propenyl]-phenyl]-acetamide, wherein the aprotic solvent used for the reaction is dimethyl formamide, dimethyl acetamide, dimethyl sulfoxide or N-methylpyrrolidone;
   ii. condensing N-ethyl-[3-[3-(dimethylamino)-1-oxo-2-propenyl]phenyl]-acetamide and 3-amino-4-cyanopyrazole, wherein the condensing is done in the presence of (a) a water immiscible organic acid, wherein the water immiscible acid used for the condensation reaction is edetic acid, fumaric acid, salicyclic acid or benzoic acid; (b) a cation exchange resin; or (c) a water miscible organic acid in water or in a C-1 to C-4 alcohol or in a mixture of water and a C-1 to C-4 alcohol; and
   iii. isolating zaleplon from the reaction.

3. A process for making zaleplon, comprising:
   i. alkylating 3-[3-(dimethylamino)-1-oxo-2-propenyl]-phenyl]-acetamide with ethyl iodide in the presence of an alkali metal hydroxide or alkoxide selected from sodium hydroxide, potassium hydroxide, sodium methoxide, sodium tert-butoxide or potassium tert-butoxide in an aprotic solvent to give N-ethyl-[3-[3-(dimethylamino)-1-oxo-2-propenyl]-phenyl]-acetamide;
   ii. condensing N-ethyl-[3-[3-(dimethylamino)-1-oxo-2-propenyl]phenyl]-acetamide; and 3-amino-4-cyanopyrazole, wherein the condensing is done in the presence of (a) a water immiscible organic acid, wherein the water immiscible acid used for the condensation reaction is edetic acid, fumaric acid, salicyclic acid or benzoic acid; (b) a cation exchange resin; or (c) a water miscible organic acid in water or in a C-1 to C-4 alcohol or in a mixture of water and a C-1 to C-4 alcohol, wherein a solvent used for the reaction is water, methanol, ethanol, isopropanol or a mixture of one or more thereof; and
   iii. isolating zaleplon from the reaction.

4. A process for making zaleplon, comprising:
   i. alkylating 3-[3-(dimethylamino)-1-oxo-2-propenyl]-phenyl]-acetamide with ethyl iodide in the presence of an alkali metal hydroxide or alkoxide selected from sodium hydroxide, potassium hydroxide, sodium methoxide, sodium tert-butoxide or potassium tert-butoxide in an aprotic solvent to give N-ethyl-[3-[3-(dimethylamino)-1-oxo-2-propenyl]-phenyl]-acetamide, wherein the aprotic solvent used for the reaction is dimethyl formamide, dimethyl acetamide, dimethyl sulfoxide or N-methyl pyrrolidone;
   ii. condensing N-ethyl-[3-[3-(dimethylamino)-1-oxo-2-propenyl]phenyl]-acetamide and 3-amino-4-cyanopyrazole, wherein the condensing is done in the presence of (a) a water immiscible organic acid, wherein the water immiscible acid used for the condensation reaction is edetic acid, fumaric acid, salicyclic acid or benzoic acid; (b) a cation exchange resin; or (c) a water miscible organic acid in water or in a C-1 to C-4 alcohol or in a mixture of water and a C-1 to C-4 alcohol, wherein a solvent used for the reaction is water, methanol, ethanol, isopropanol or a mixture of one or more thereof; and iii. isolating zaleplon from the reaction.

5. The process according to claim 2, wherein the cation exchange resin used is a strong cation exchange resin in the $H^+$ form.

6. The process according to claim 2, wherein the cation exchange resin used is a strong cation exchange resin in the $H^+$ form.

7. The process according to claim 5, wherein the reaction is carried out in a solvent which is water, methanol, ethanol, isopropanol or a mixture of one or more thereof.

8. The process according to claim 6, wherein the reaction is carried out in a solvent which is water, methanol, ethanol, isopropanol or a mixture of one or more thereof.

9. The process according to claim 1, wherein the water miscible organic acid is formic acid, maleic acid, tartaric acid, citric acid, oxalic acid, or succinic acid.

10. The process according to claim 2, wherein the water miscible organic acid is formic acid, maleic acid, tartaric acid, citric acid, oxalic acid, or succinic acid.

11. The process according to claim 9, wherein the condensing is done in a mixture of a C1 to C4 alcohol and water at ambient to reflux temperature.

12. The process according to claim 10, wherein the condensing is done in a mixture of a C1 to C4 alcohol and water at ambient to reflux temperature.

13. The process according to claim 11, wherein the percentage of water in alcohol by weight ranges from 0.5% to 9.5%.

14. The process according to claim 12, wherein the percentage of water in alcohol by weight ranges from 0.5% to 9.5%.

15. The process according to claim 13, wherein the alcohol used is methanol, ethanol or isopropanol.

16. The process according to claim 14, wherein the alcohol used is methanol, ethanol or isopropanol.

17. The process according to claim 3, wherein the cation exchange resin used is a strong cation exchange resin in the $H^+$ form.

18. The process according to claim 4, wherein the cation exchange resin used is a strong cation exchange resin in the $H^+$ form.

19. The process according to claim 3, wherein the water miscible organic acid is formic acid, maleic acid, tartaric acid, citric acid, oxalic acid, or succinic acid.

* * * * *

UNITED STATES PATENT AND TRADEMARK OFFICE
CERTIFICATE OF CORRECTION

PATENT NO. : 7,772,394 B2
APPLICATION NO. : 10/570453
DATED : August 10, 2010
INVENTOR(S) : Rajendra Narayanrao Kankan et al.

It is certified that error appears in the above-identified patent and that said Letters Patent is hereby corrected as shown below:

Column 7, Line 8, Claim 5, replace "The process according to claim 2 wherein" with -- The process according to claim 1 wherein --

Signed and Sealed this

Twelfth Day of October, 2010

David J. Kappos
*Director of the United States Patent and Trademark Office*